United States Patent
Baust et al.

(10) Patent No.: US 11,419,656 B2
(45) Date of Patent: Aug. 23, 2022

(54) THERMAL REGULATION CATHETER SYSTEM

(71) Applicant: CPSI Holdings LLC, Owego, NY (US)

(72) Inventors: John M. Baust, Owego, NY (US); Jennie F. McKain, Endicott, NY (US); Anthony T. Robilotto, Binghamton, NY (US); Joshua T. Smith, Owego, NY (US)

(73) Assignee: CPSI Holdings LLC, Owego, NY (US)

( * ) Notice: Subject to any disclaimer, the term of this patent is extended or adjusted under 35 U.S.C. 154(b) by 327 days.

(21) Appl. No.: 14/678,393

(22) Filed: Apr. 3, 2015

(65) Prior Publication Data

US 2015/0282858 A1   Oct. 8, 2015

Related U.S. Application Data

(60) Provisional application No. 61/975,383, filed on Apr. 4, 2014.

(51) Int. Cl.
*A61B 18/02* (2006.01)
*A61B 18/00* (2006.01)

(52) U.S. Cl.
CPC ..... *A61B 18/02* (2013.01); *A61B 2018/00011* (2013.01); *A61B 2018/0025* (2013.01);
(Continued)

(58) Field of Classification Search
CPC .......... A61B 18/02; A61B 2018/00011; A61B 2018/00041; A61B 2018/00166; A61B 2018/00172; A61B 2018/0025; A61B 2018/00351; A61B 2018/00488; A61B 2018/00577; A61B 2018/00791; A61B 2018/00863; A61B 2018/00875; A61B 2018/0212; A61B 2018/0262; A61B 2018/0281; A61B 2018/0022;
(Continued)

(56) References Cited

U.S. PATENT DOCUMENTS 3,425,419 A * 2/1969 Dato ................. A61B 1/12
606/22
4,729,763 A * 3/1988 Henrie ........... A61B 17/320758
604/22

(Continued)

OTHER PUBLICATIONS

Arruda et al., "Feasibility and Safety of Using an Esophageal Protective System to Eliminate Esophageal Thermal Injury: Implications on Atrial-Esophageal Fistula Following AF Ablation," J Cardiovasc Electrophysiol. 20(11):1272-8 (2009).

(Continued)

*Primary Examiner* — Ronald Hupczey, Jr.
(74) *Attorney, Agent, or Firm* — Hoffman Warnick LLC

(57) ABSTRACT

A thermal regulation catheter system and method of use are disclosed, for moderating the temperature and other parameters of tissue surrounding a target tissue for an ablation procedure, or for performing a thermal treatment procedure. In an embodiment, the device includes a catheter having a shaft with a fluid supply line and a fluid return line disposed therein, and an inflatable heat exchange vessel at a distal end of the shaft. The fluid supply line supplies fluid to inflate the heat exchange vessel, and the fluid return line conducts fluid away from the heat exchange vessel.

23 Claims, 13 Drawing Sheets

(52) U.S. Cl.
CPC ............... *A61B 2018/00041* (2013.01); *A61B 2018/00166* (2013.01); *A61B 2018/00172* (2013.01); *A61B 2018/00351* (2013.01); *A61B 2018/00488* (2013.01); *A61B 2018/00577* (2013.01); *A61B 2018/00791* (2013.01); *A61B 2018/00863* (2013.01); *A61B 2018/00875* (2013.01); *A61B 2018/0212* (2013.01); *A61B 2018/0262* (2013.01); *A61B 2018/0281* (2013.01)

(58) Field of Classification Search
CPC ........... A61B 2017/22051; A61B 2018/00005; A61B 2018/00214; A61B 2018/00255; A61B 2018/00261; A61B 2018/0074; A61B 18/04; A61B 2018/044; A61B 2018/046; A61F 2007/0054; A61F 2007/0055; A61F 7/12; A61F 7/123; A61F 2007/126
USPC .......................................................... 606/21
See application file for complete search history.

(56) References Cited

U.S. PATENT DOCUMENTS

| | | | | |
|---|---|---|---|---|
| 5,212,953 | A * | 5/1993 | Kawaguchi | F17C 13/026 250/370.15 |
| 5,215,523 | A * | 6/1993 | Williams | A61B 1/00048 604/100.03 |
| 5,281,215 | A * | 1/1994 | Milder | A61B 18/02 606/20 |
| 6,042,559 | A * | 3/2000 | Dobak, III | A61M 1/369 604/113 |
| 6,635,053 | B1 * | 10/2003 | Lalonde | A61B 18/02 606/22 |
| 6,746,445 | B2 * | 6/2004 | Abboud | A61B 18/02 606/20 |
| 7,220,226 | B2 * | 5/2007 | Rovegno | A61B 1/012 600/104 |
| 7,621,908 | B2 | 11/2009 | Miller | |
| 8,224,422 | B2 | 7/2012 | Mottola et al. | |
| 8,382,747 | B2 * | 2/2013 | Abboud | A61M 25/10185 606/22 |
| 8,454,588 | B2 | 6/2013 | Rieker et al. | |
| 8,690,826 | B2 * | 4/2014 | Noda | F04C 29/0064 604/113 |
| 9,351,869 | B2 * | 5/2016 | Knott | A61M 1/369 |
| 2002/0007180 | A1 * | 1/2002 | Wittenberger | A61B 18/02 606/21 |
| 2008/0033415 | A1 | 2/2008 | Rieker et al. | |
| 2008/0161890 | A1 * | 7/2008 | Lafontaine | A61B 18/1492 607/105 |
| 2010/0121270 | A1 * | 5/2010 | Gunday | A61B 17/22012 604/98.01 |
| 2010/0179537 | A1 | 7/2010 | Rashidi | |
| 2011/0082488 | A1 | 4/2011 | Niazi | |
| 2011/0282338 | A1 | 11/2011 | Fojtik | |
| 2012/0029495 | A1 * | 2/2012 | Wittenberger | A61B 18/02 606/21 |
| 2013/0006139 | A1 | 1/2013 | Tiano | |
| 2014/0074081 | A1 | 3/2014 | Burnett et al. | |
| 2014/0088579 | A1 * | 3/2014 | Burnett | A61B 18/02 606/21 |

OTHER PUBLICATIONS

Carroll et al., "Multi-Sensor Esophageal Temperature Probe Used During Radiofrequency Ablation for Atrial Fibrillation is Associated with Increased Intraluminal Temperature Detection and Increased Risk of Esophageal Injury Compared to Single-Sensor Probe," J Cardiovasc Electrophysiol. 24(9):958-64 (2013).

Kanjwal et al., "Retro-cardiac esophageal mobility and deflection to prevent thermal injury during atrial fibrillation ablation: an anatomic feasibility study," J Interv Card Electrophysiol. 30(1):45-53 (2011).

* cited by examiner

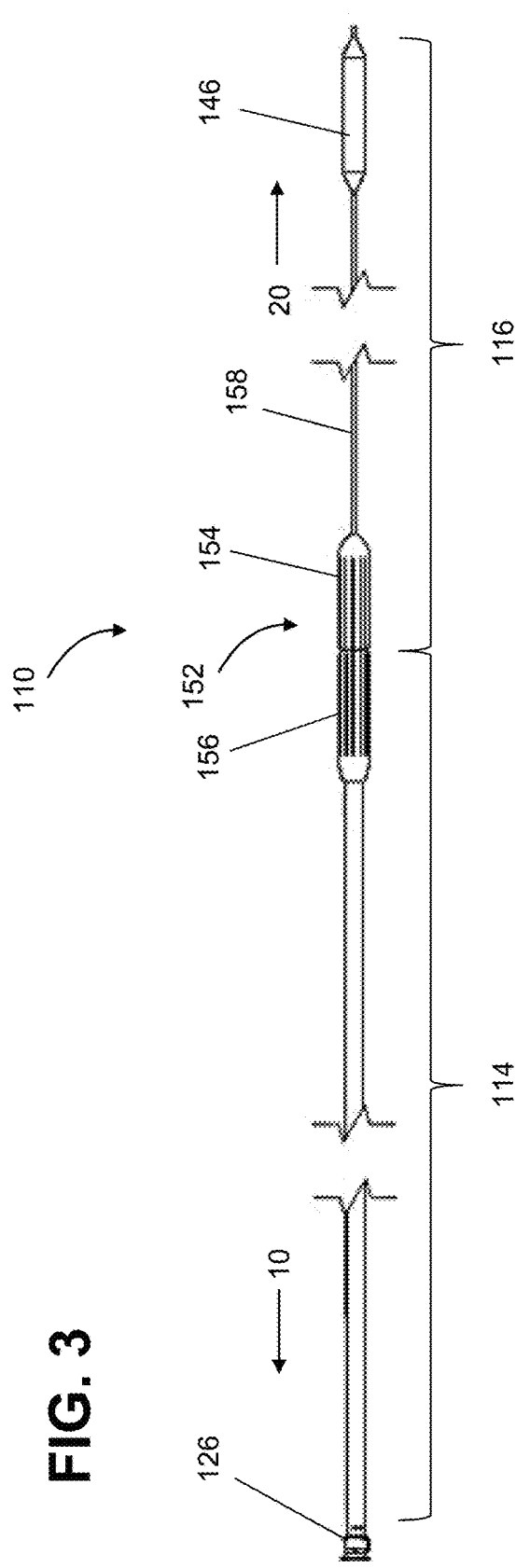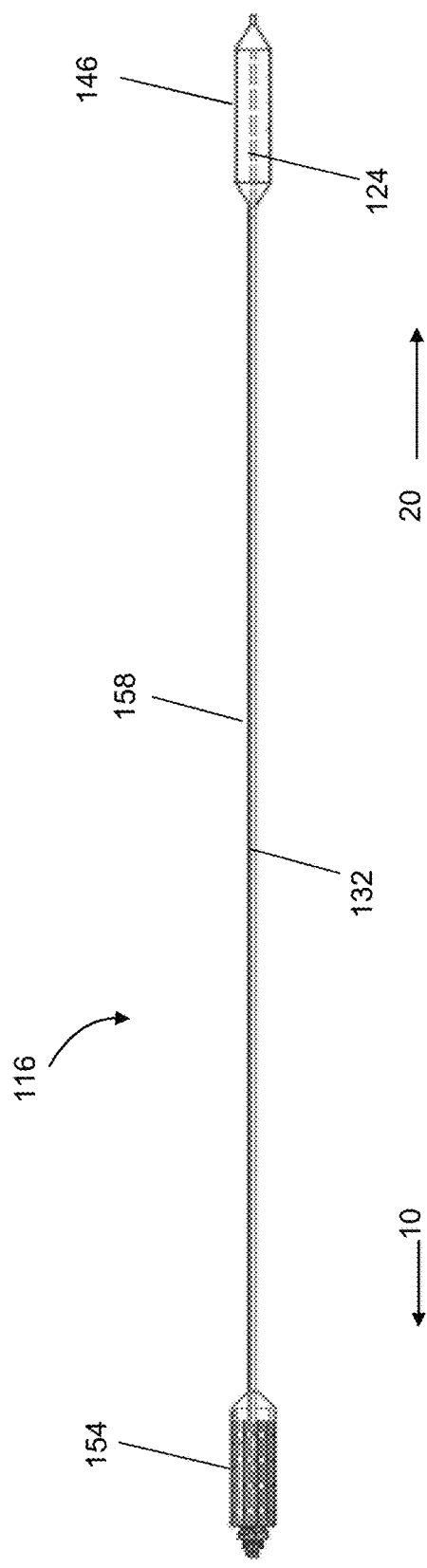
FIG. 3
FIG. 4A

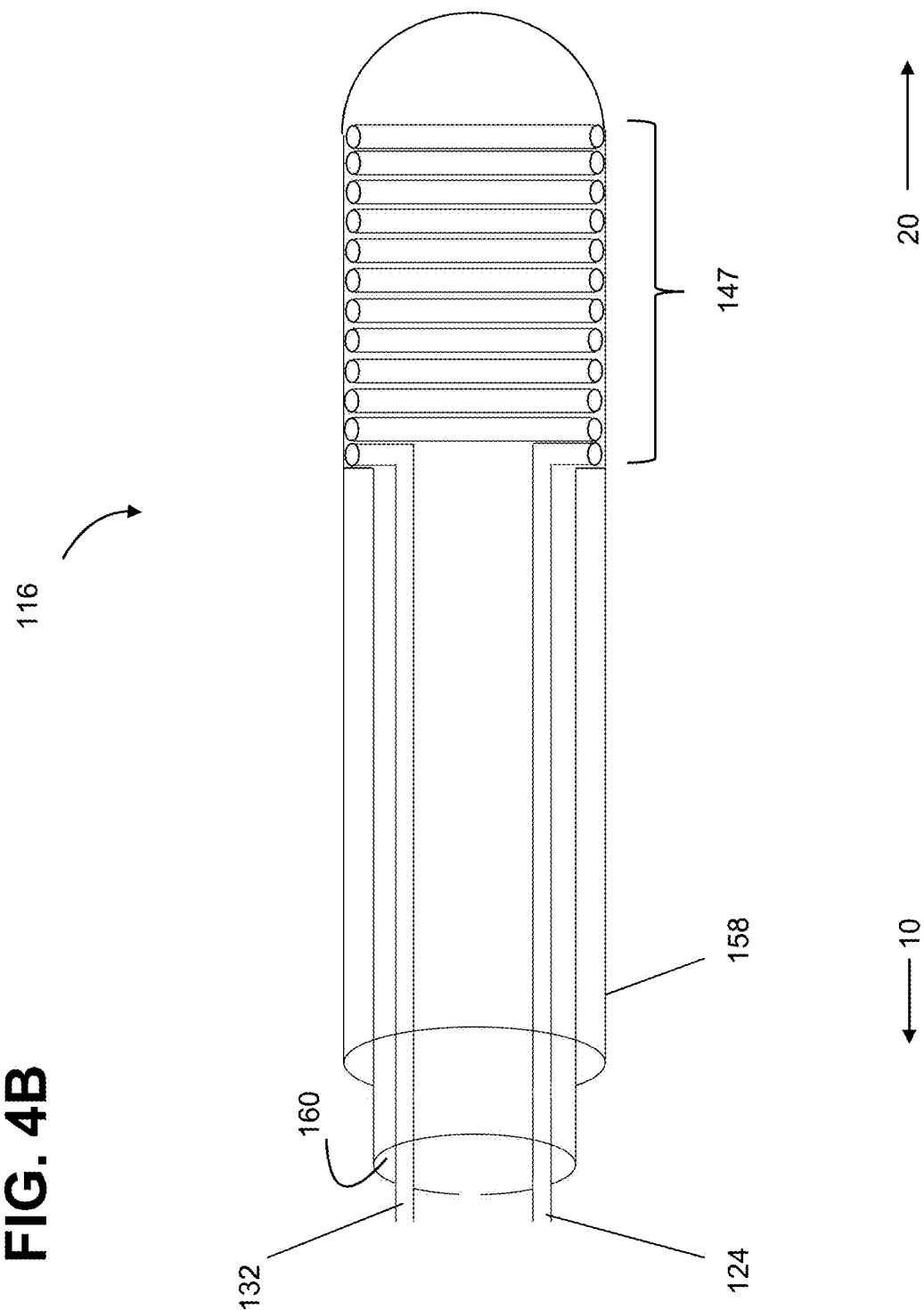

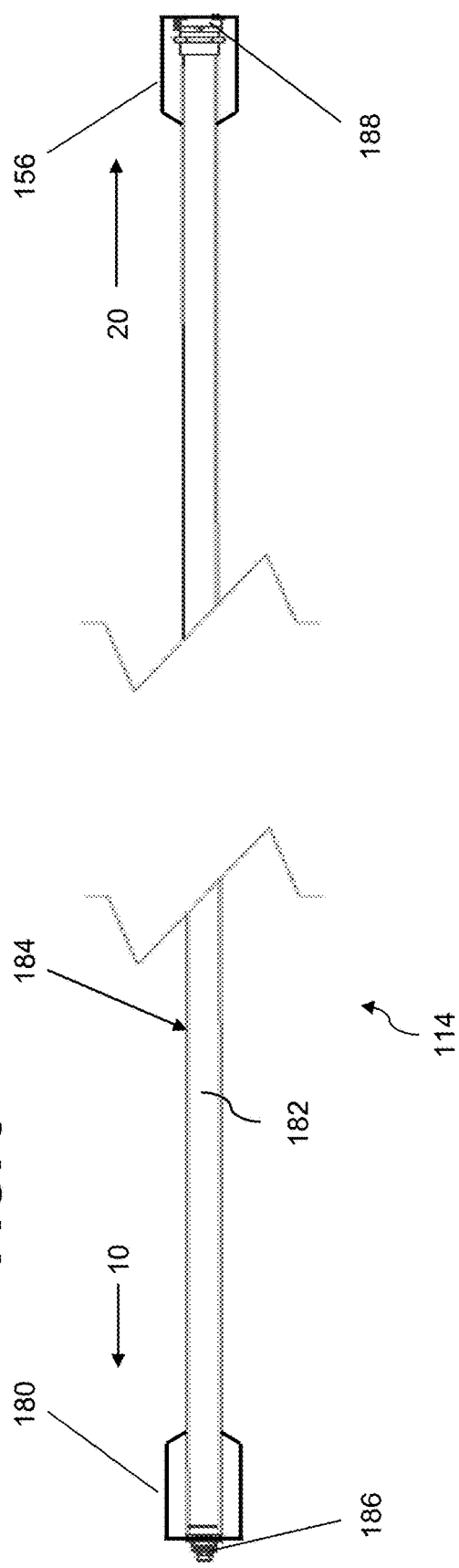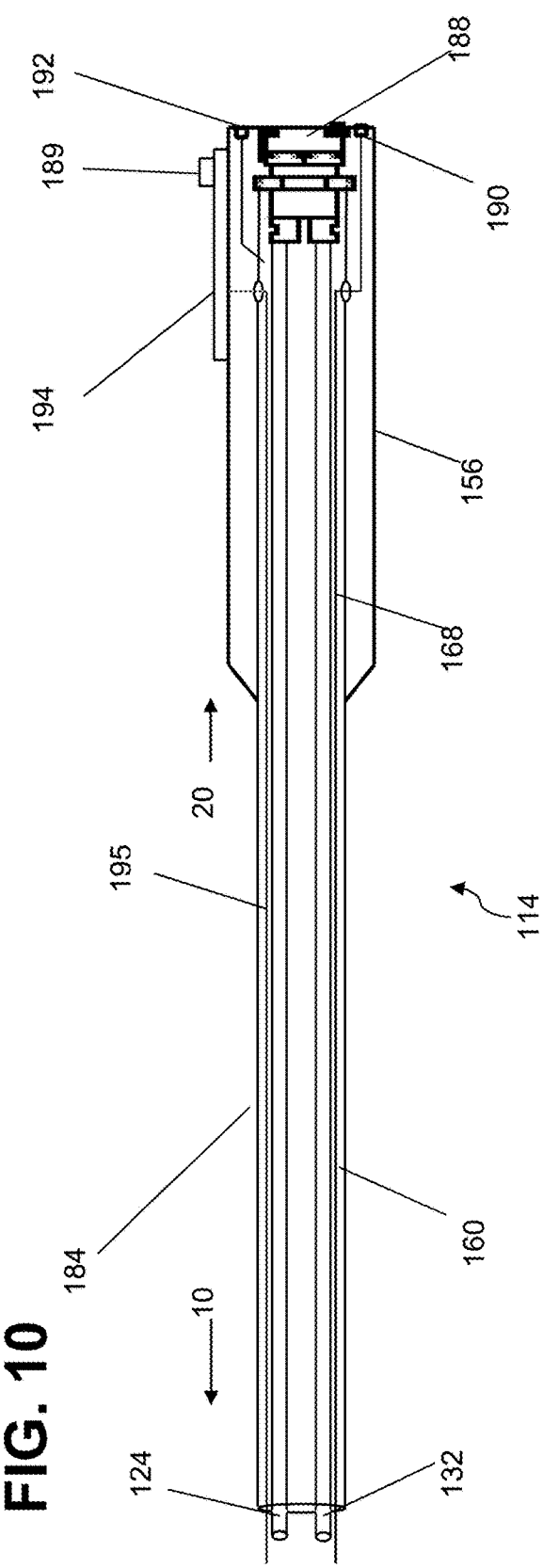

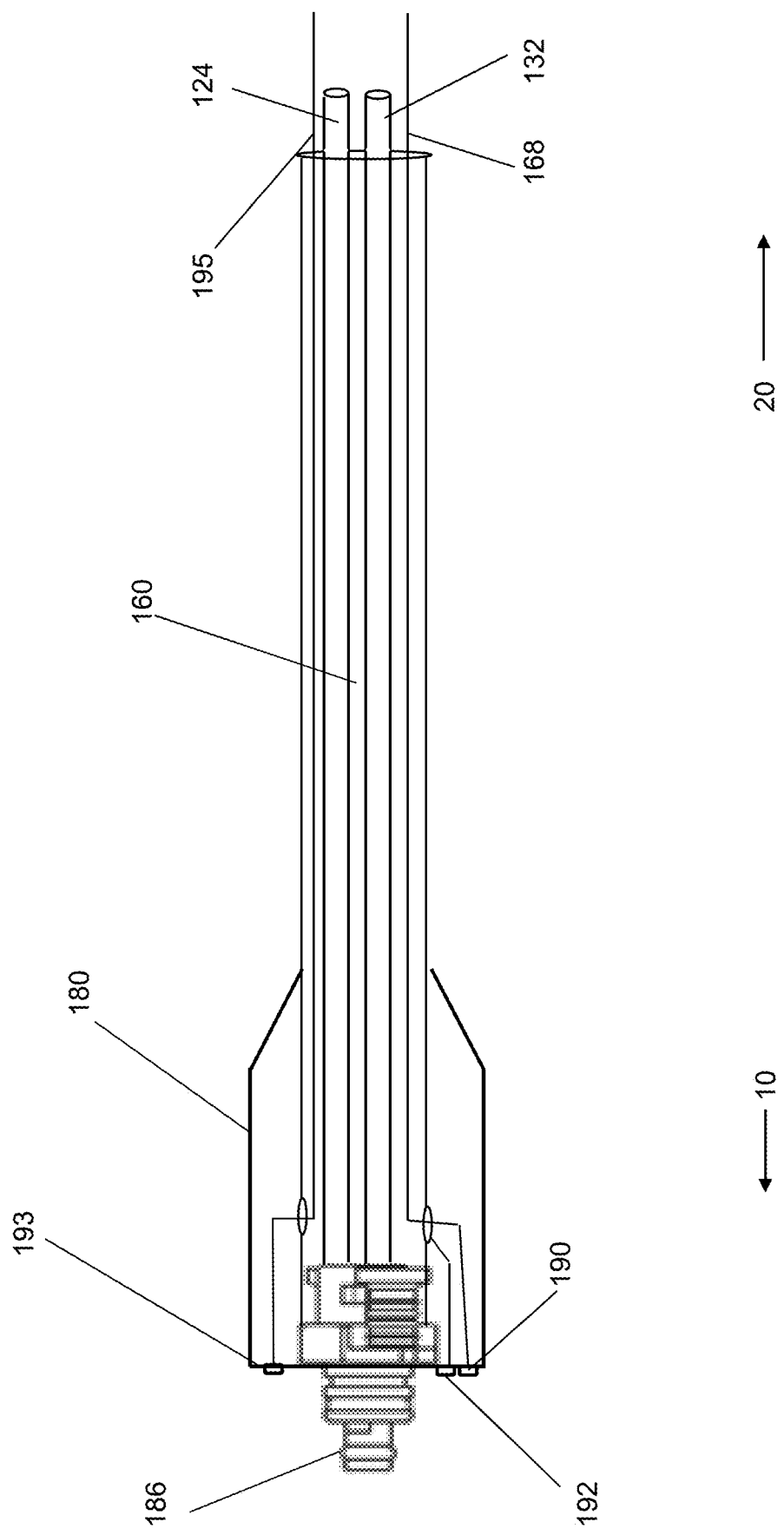

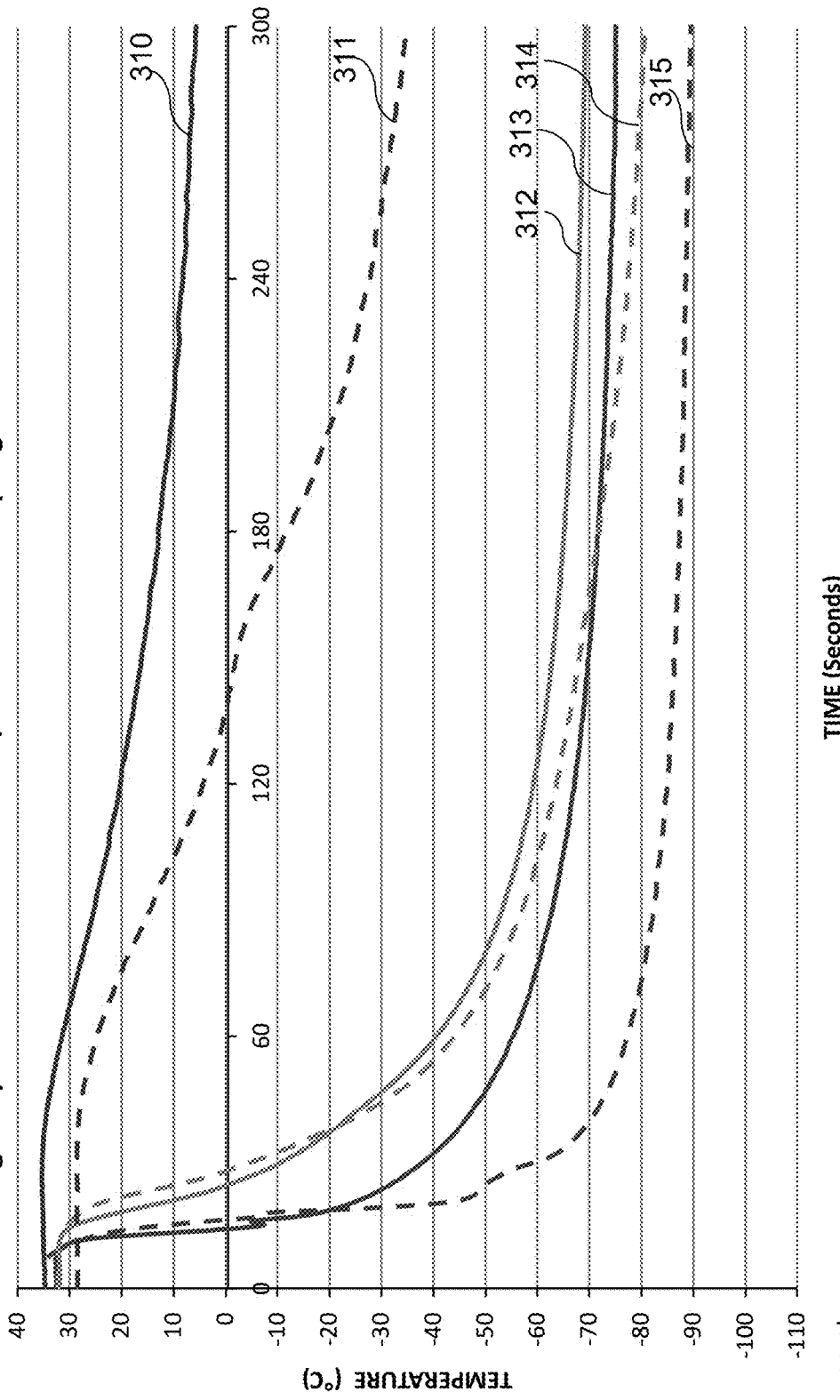

THERMAL REGULATION CATHETER SYSTEM

CROSS-REFERENCE TO RELATED APPLICATIONS

This application claims benefit of U.S. Provisional Patent Application No. 61/975,383, filed Apr. 4, 2014, which is hereby incorporated herein.

BACKGROUND OF THE INVENTION

The invention relates generally to protection of tissue surrounding a target tissue in an ablation procedure. More particularly, the invention relates to a device and method for protecting esophageal tissue during cardiac ablation procedures.

Currently, approximately 350,000 individuals are diagnosed with, 460,000 individuals are hospitalized for, and 80,000 deaths are attributable to atrial fibrillation annually in the United States. Overall there are 4 million individuals in the US with atrial fibrillation, with a projected increase to 10-12 million within the next 20 years. In the US alone, billions of dollars are spent annually to manage cardiac arrhythmias. Despite advances, a high mortality rate remains.

The standard treatment for patients with arrhythmias is drug therapy, although drugs are effective in only approximately 50% of patients. As such, there has been a steady increase in the use of ablative therapies, such as radio frequency (RF), High-Intensity Focused Ultrasound (HIFU), and cryoablation, to treat various cardiac arrhythmias. It is projected that approximately 20% of the patients hospitalized for atrial fibrillation in 2014—received some form of cardiac ablation therapy.

Damage and changes in the esophagus are a common and concerning side effect as cardiac ablation therapy procedures continue to increase. In 2012 Qumseya, et al. and others reported that esophageal alterations following cardiac ablation therapy occur in 47-49% of patients. This suggests that more than 50,000 patients experienced esophageal injury in 2014 alone. To date the development of devices and approaches to prevent, diagnose, and treat esophageal injury and atrialesophageal fistula (a hole between the heart and esophagus) have been limited due to the difficulty in diagnosis, unusual occurrence rate and limited studies. The primary strategy to prevent esophageal damage is to reduce the power, time, or number of ablations during cardiac ablation therapy. While effective at reducing esophageal injury, this incomplete application of thermal energy is responsible for much of the >40% rate of arrhythmia reoccurrence associated with cardiac ablation therapy.

Current devices and strategies to monitor and limit esophageal damage include thermal monitoring devices and mechanical deflection of the esophagus away from the atria during ablation procedures. Recently, Arrunda et al. have demonstrated the potential of cooling the esophagus (EPSac (esophageal protective system) device) during RF ablation to limit injury. This report illustrated the potential of esophageal protection strategies. Given the high mortality of atrialesophageal fistula coupled with the continued rise in the use of cardiac ablation therapy, there is a compelling need for the development of new strategies and technologies to prevent esophageal injury and atrialesophageal fistula.

In situ ablation of cardiac tissue has been shown to be highly effective for the treatment of atrial fibrillation, yet concerns relating to collateral damage to surrounding tissue and has limited its growth. Further, with the increased use of cardiac ablation therapy, concerns are mounting that increased incidence of associated esophageal injury and atrialesophageal fistula will follow. As such, a need exists for the development of new devices and treatment options to prevent esophageal injury while allowing for complete and effective cardiac tissue destruction. The ability to maintain or protect the esophagus during cardiac ablation therapy is highly desired in order to reduce tissue damage, complication risk, risk of atrialesophageal fistula, procedure time, and overall cost, among others while at the same time improving procedural efficacy.

BRIEF DESCRIPTION OF THE INVENTION

A first aspect of the disclosure provides a system for protecting surrounding tissue during an ablation procedure. In an embodiment, the system includes a reservoir configured to contain a fluid and to adjust and maintain a desired temperature of the fluid; and a catheter having a shaft and a first heat exchange vessel at a distal tip of the shaft. The catheter is fluidly connected to the reservoir by a supply line for supplying fluid from the reservoir to the first heat exchange vessel, and a return line for returning the fluid from the heat exchange vessel.

A second aspect of the disclosure provides a device for protecting surrounding tissue during an ablation procedure. In an embodiment, the device includes a catheter including: a shaft having a fluid supply line and a fluid return line disposed therein, and an inflatable heat exchange vessel at a distal end of the shaft. The fluid supply line supplies fluid to inflate the heat exchange vessel, and the fluid return line conducts fluid away from the heat exchange vessel.

A third aspect of the disclosure provides a method of moderating a temperature of surrounding tissues during an ablation procedure. In an embodiment, the method includes providing a device that includes a catheter including a shaft having a fluid supply line and a fluid return line disposed therein, and an inflatable heat exchange tip at a distal end of the shaft, wherein the fluid supply line supplies fluid to inflate the heat exchange tip, and the fluid return line conducts fluid away from the heat exchange tip. The method further includes inserting the device into the surrounding tissue such that the heat exchange tip contacts the surrounding tissue; filling the heat exchange tip with a temperature-controlled fluid; and circulating the temperature-controlled fluid through a closed loop system that includes the heat exchange tip.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

FIG. 3 is an illustrative view of the umbilical and catheter according to an embodiment of the invention.

FIGS. 4A-B are illustrations of catheters according to embodiments of the invention.

FIG. 9 is an illustrative overview of the umbilical according to an embodiment of the invention.

FIG. 10 is an illustrative view of the distal end of the umbilical handle wherein the catheter interconnects with the umbilical according to an embodiment of the invention.

FIG. 11 is an illustrative view of the proximal end handle of the umbilical which interconnects with the console according to an embodiment of the invention.

FIG. 17 is a graphic representation of the thermal protection ability of the system when used during a cryoablation procedure performed in an ex vivo porcine tissue model.

Figure 1:
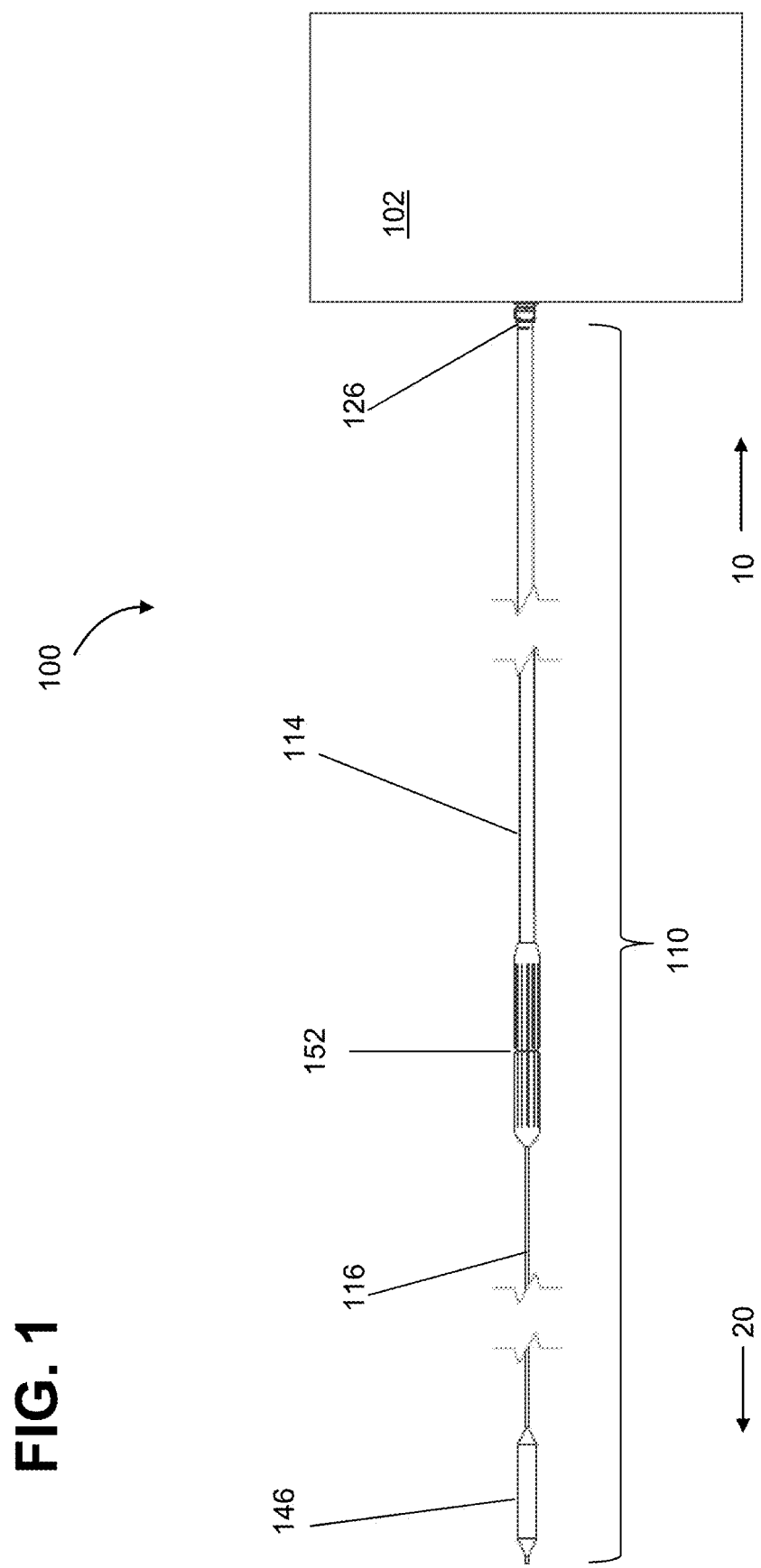
FIG. 1 depicts an illustrative embodiment of the system of the present invention including the console, umbilical and catheter.

These and other aspects, advantages, and salient features of the invention will become apparent from the following detailed description, which, when taken in conjunction with the annexed drawings, where like parts are designated by like reference characters throughout the drawings, disclose embodiments of the invention.

DETAILED DESCRIPTION

At least one embodiment of the present thermal regulation catheter system is described below in reference to its application in connection with cardiac ablation procedures. Although embodiments of the invention are illustrated relative to protection of esophageal tissue during cardiac ablation procedures and performance of ablation procedures, it is understood that the teachings are equally applicable to protection or ablation of other types of tissue during other types of procedures. Further, at least one embodiment of the present invention is described below in reference to a nominal size and including a set of nominal dimensions. However, it should be apparent to those skilled in the art that the present invention is likewise applicable to any suitable protection device and/or probe. Further, it should be apparent to those skilled in the art that the present invention is likewise applicable to various scales of the nominal size and/or nominal dimensions.

As indicated above, aspects of the invention provide a system and medical device for maintaining, monitoring, and regulating thermal conditions in tissues, and delivering a temperature controlled fluid to various configurations of a probe or catheter for the protection of esophageal or other non-targeted tissues from damage during a thermal ablation (heat or cryo) procedure. FIGS. 1-17 show different aspects of a thermal regulation catheter system 100 in accordance with various embodiments of the invention.

FIG. 1 shows an external overview of the thermal regulation catheter system 100, including console 102 and operational device 110, which includes umbilical 114, and catheter 116, in accordance with an embodiment of the present invention. It is noted that umbilical 114, as used herein, refers to any type of flexible or inflexible tube, hose, cable, or grouping of tubes, hoses, or cables, for connecting the console 102 and catheter 116, and providing the functions described herein.

Figure 2:
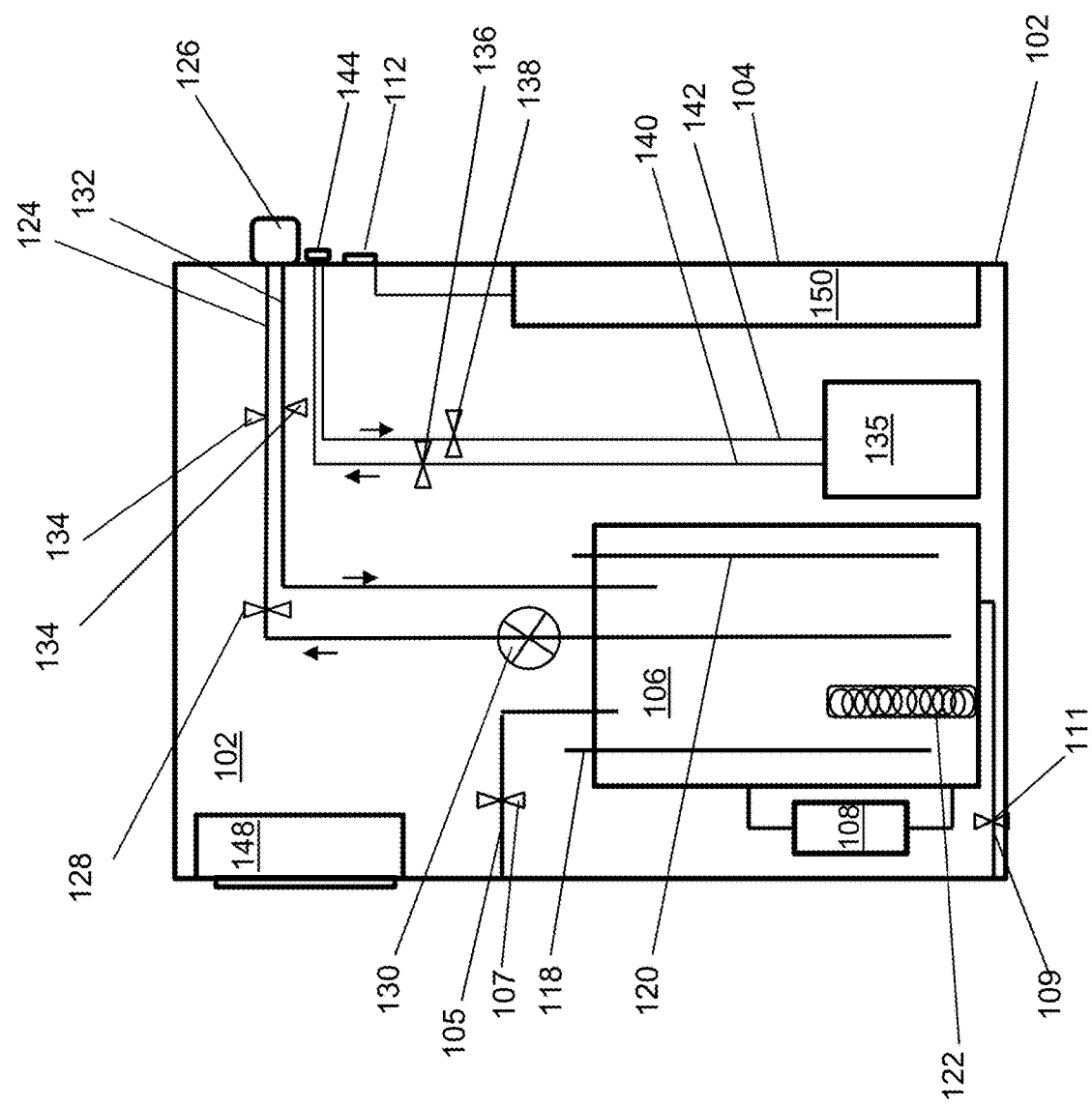
FIG. 2 is a side view of the console and components including the reservoir, control panel, connection ports, plumbing and wiring according to an embodiment of the invention.

Console 102 of thermal regulation catheter system 100 may include sidewalls 104 forming an enclosure for the device, shown in greater detail in FIG. 2. In one embodiment, console 102 may contain the mechanical and electrical mechanisms of the operational device 110, allowing the system 100 to be easily transported. The console 102 enclosure may include any mobile feature such as wheels, handles, and fixtures (or may allow placement onto a cart having these features) so that the system 100 can be transported to and from the location of treatment. Such mobility allows the system to be easily moved to and from an operating room or site of therapeutic treatment.

As shown in FIG. 2, within the console 102 enclosure, a fluid reservoir 106 may be provided, which includes a heating and/or cooling element and circulation pump 108, all of which are programmable and controllable to facilitate heating or cooling of the fluid within reservoir 106 to a desired temperature. The fluid level within the reservoir 106 is monitored by a level sensor 118 and fluid temperature is monitored by a temperature sensor 120 within the reservoir 106. Reservoir fill line 105 with fill valve 107 is provided for filling reservoir 106, and reservoir drain line 109 with drain valve 111 is provided for draining reservoir 106. A supplemental heating and cooling coil 122 may also be contained within the reservoir 106 to allow for rapid real-time adjustment of fluid temperature during operation. In another embodiment (not shown), fluid reservoir 106 may be an external source such as an IV bag or other fluid container, and the fluid heating and cooling mechanism may include a heat transfer coil or plate within console 102. The heat exchange plate or coil may consist of a solid plate with a fluid path (tube or cartridge) contained within a plate or coil placed within a separate heating or cooling reservoir within console 102. The heat exchange plate or coil fluid path may be an integrated or disposable cartridge within the heat exchange apparatus. The fluid may then flow through the heat exchange plate or cartridge then to the catheter 116 as in FIG. 1.

Referring back to FIG. 2, connected to the output of the reservoir 106 is a supply line 124 through which fluid flows from the reservoir 106 to the umbilical connection port 126 on an exterior of sidewall 104 of console 102. Flow of the fluid through the supply line 124 to the catheter 116 via umbilical 114 is controlled by a flow control valve 128, and the rate of flow is controlled by fluid supply pump 130. This pump 130 may be integrated into, or may be separate from the fluid reservoir 106. After the fluid travels out of the console 102 to the catheter 116, the fluid is returned from the catheter 116 to the reservoir 106 via a return line 132 forming a closed loop system within the console 102. The temperature and flow rate of the fluid in the supply and return lines 124, 132 (i.e., the flow rate going to and returning from the catheter 116) is monitored by a series of sensors 134 located along each line 124, 132.

The console 102 may also contain an inflation/deflation vacuum pump 135 coupled to a connection port 144 on the exterior of sidewall 104 of console 102 by inflation line 140 and vacuum line 142, which may include a series of control valves 136, 138 for facilitating inflation and deflation of the balloon-like distal heat exchange vessel element (i.e., "balloon") 146 at the distal end of the catheter 116.

The operation of console 102 and monitoring of the various sensors 118, 120, 134 in the console 102 as well as the umbilical 114 and catheter 116, and sensors 166 therein (FIG. 5) are controlled by the system control and monitoring center 148 and the electronic control circuitry of the system contained within the electronic control panel 150. The thermal regulation catheter system 100 may be controlled and operated by a series of electronic or manual buttons, knobs, switches, or other control devices located within the system control and monitoring center 148. The system control and monitoring center 148 may further include a computing device including a control software program stored in a memory thereof, which when executed, carries out various control and monitoring functions of the system as discussed further below with respect to FIG. 12.

As shown in FIG. 1, an umbilical 114 and catheter assembly 116 are connected to the console 102 at umbilical connection port 126. The umbilical 114 and catheter assembly 116 are shown separately from the console 102 and in greater detail in FIG. 3. The proximal end 10 of the umbilical 114 connects to the console 102 via connection port 126, which may include, e.g., a quick disconnect or other means of connection (FIG. 2). Console 102 may also include vacuum and inflation connection port 144, and sensor connection port 112, which are discussed in further detail below. At the distal end 20 of the umbilical 114 there is a handle assembly 152, in which the proximal handle end 154 of the catheter 116 interconnects via quick connection or other type of connector with the distal handle end 156 of the umbilical 114. The interconnection of the catheter 116 to the console 102 via umbilical 114 allows for the delivery of temperature controlled fluid from the console 102 reservoir 106 to the distal heat exchange end/vessel (balloon) 146 of the catheter 116 and the return of the fluid to the reservoir 106 within the console 102.

The catheter 116 portion of the system, shown in FIG. 4A, consists of a handle 154 at the proximal end, a catheter shaft 158, and a heat exchange region 146 at the distal end 20. Heat exchange region 146 may have a balloon-like distal tip, and may be referred to as balloon 146. The balloon 146 may be, in some embodiments, about 1 cm to about 4 cm in diameter, and about 5 cm to about 20 cm in length. The balloon-like tip may be compliant, semi-compliant or non-compliant in nature. In another embodiment, shown in FIG. 4B, the catheter 116 may have a solid, coiled, or multi-lumen tip, such as coiled thermal maintenance region 147, which serves as the heat exchange surface in lieu of the previously-described balloon 146. In such an embodiment, the catheter tip may be a tube having an open lumen(s), where fluid comes into contact with the outer tube forming the heat exchange region. In the case of a coil, as illustrated in FIG. 4B, there may be a tube coiled within the heat exchange region 147, which may be inside and in contact with the catheter shaft 158, thereby creating a heat exchange surface.

Figure 5:
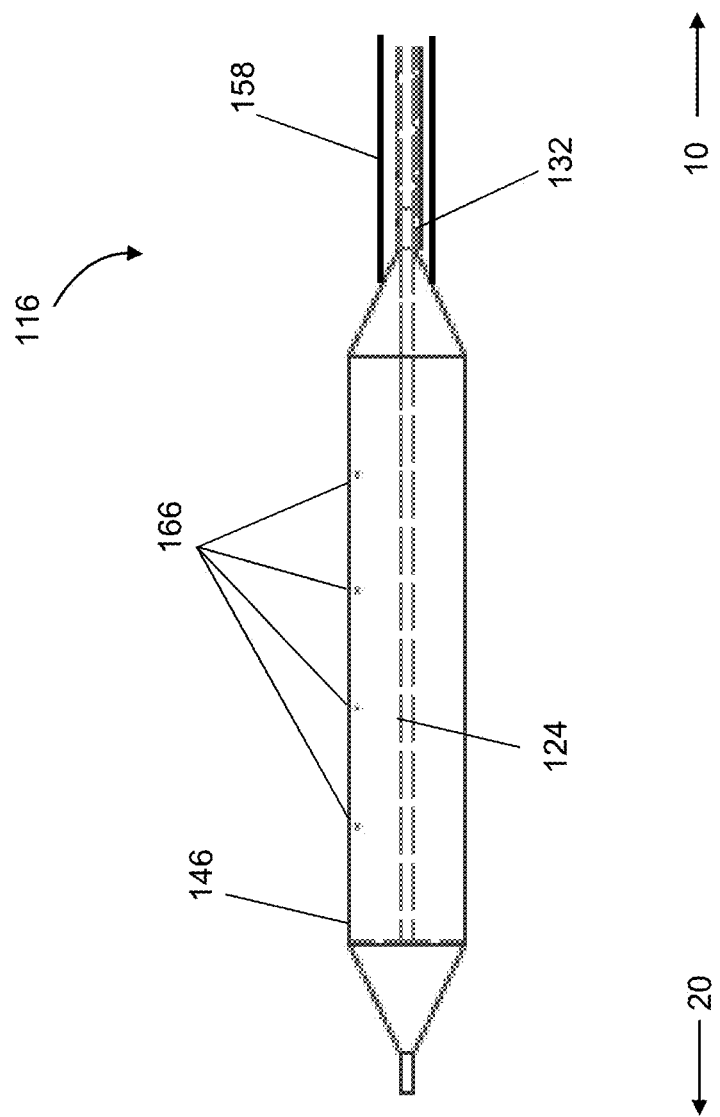
FIG. 5 is an illustration of the distal heat exchange region of the catheter with a balloon-like tip according to an embodiment of the invention.

Catheter 116 may further include supply and return lines 124, 132 respectively, which may be configured in a coaxial or side by side configuration depending on the design. In one embodiment (e.g., FIG. 8), a supply line 124 and a return line 132 are enclosed within the outer sheath 164 of the catheter 116, and are substantially parallel to one another. In another embodiment featuring a coaxial arrangement of the supply and return lines 124, 132, the return line 132 and catheter 116 may be the same tube, as shown in FIGS. 5 and 6, and the supply line 124 may be substantially concentric with the return line 132 and may be disposed within the return line 132.

At the distal end 20 of the catheter 116, the balloon-like heat exchange vessel 146 (or coiled thermal maintenance region 147) is attached to the supply and return lines 124, 132 and catheter shaft 158. Regardless of the configuration chosen, the supply line 124 runs into the heat exchange vessel 146 to allow for delivery of the fluid into the heat exchange vessel 146 and return of the fluid via the return line 132. Within the heat exchange vessel 146 at the catheter tip, a series of sensors 166 may be placed at various intervals within or along either the inner or outer surface or within the wall of the catheter shaft 158 or heat exchange vessel 146. The sensors 166 may include temperature sensors, which may be thermocouples or other sensors as known in the art, or other types of sensors such as, e.g., pressure, flow, electrical conduction, electrical impedance, acoustic, infrared, ultrasound, or visual sensors. These sensors are connected to the umbilical 114 and console 102 (via sensor connection port 112, FIG. 2) through a series of wires, fiber optics, wireless relays, or other means of communication, referred to generically herein as wires 168, contained within the catheter shaft 158, heat exchange vessel 146, and umbilical 114, as shown in FIGS. 6, 8, 10, and 11.

Figure 6:
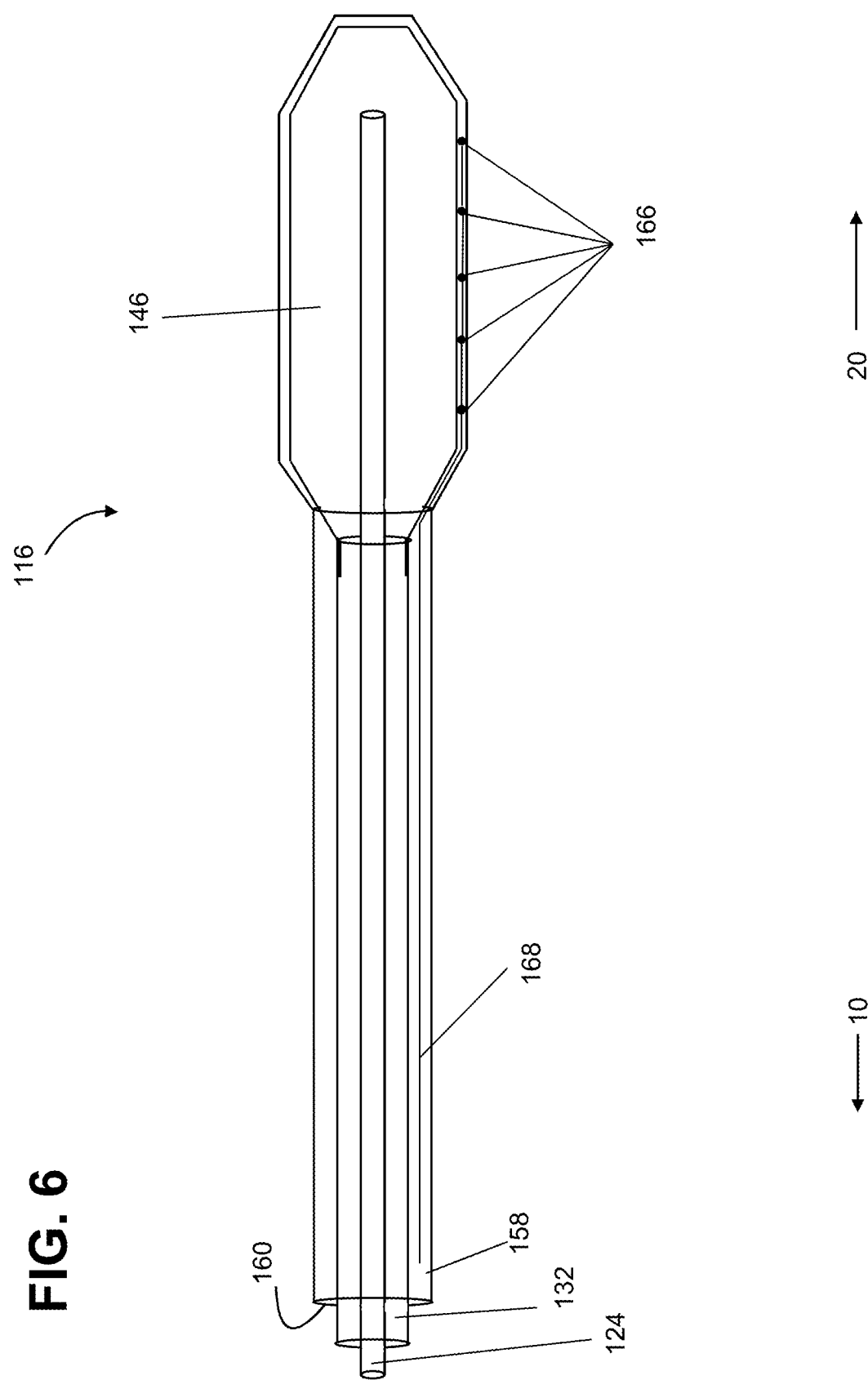
FIG. 6 is an illustrative view of the distal heat exchange tip with a double balloon configuration according to an embodiment of the invention.

In further embodiments, as shown in FIG. 6, the supply and return lines 124, 132 may be configured in a coaxial relationship such that the supply line 124 is disposed substantially concentrically within the return line 132, and the return line 132 may be disposed, again substantially concentrically, within the inner wall of the catheter shaft 158. Such an arrangement provides a lumen 160 which may be substantially annularly shaped, disposed between the outer wall of the return line 132 and inner wall of the catheter shaft 158. This lumen 160 may be fluidly coupled at the proximal end 10 to the console 102 via the umbilical 114 and vacuum/inflation port 144, and may be used to communicate gas or other fluid to and from the heat exchange vessel 146 to inflate and deflate the balloon-like heat exchange vessel 146 as desired. In some embodiments, for example, air, nitrogen, oxygen, or other gases may be pumped into or vacuumed from the balloon by the inflation/deflation pump 135 in the console 102 (FIG. 2).

In embodiments in which the heat exchange vessel 146 is in the form of a balloon, the heat-exchange balloon 146 may take any number of forms including a single layer balloon (FIGS. 3-5) bounded by a single membrane, or double layer balloon or "balloon within a balloon," membrane within a membrane configuration (FIG. 6), a flexible or rigid tube, a coil, a needle-like probe, a blunt tip probe, a flat spatula-like probe or any other configuration. Further, the catheter shaft 158 may be flexible or rigid depending on the desired features. For example, a rigid shaft may facilitate a combination of thermal protection and mechanical deflection of the esophagus away from the heart. A flexible shaft may facilitate easy insertion and removal of the catheter from the patient (FIG. 12), as it turns and flexes to accommodate the contours of, e.g., the patient's esophagus, mouth, and/or nasal passages.

Figure 7:
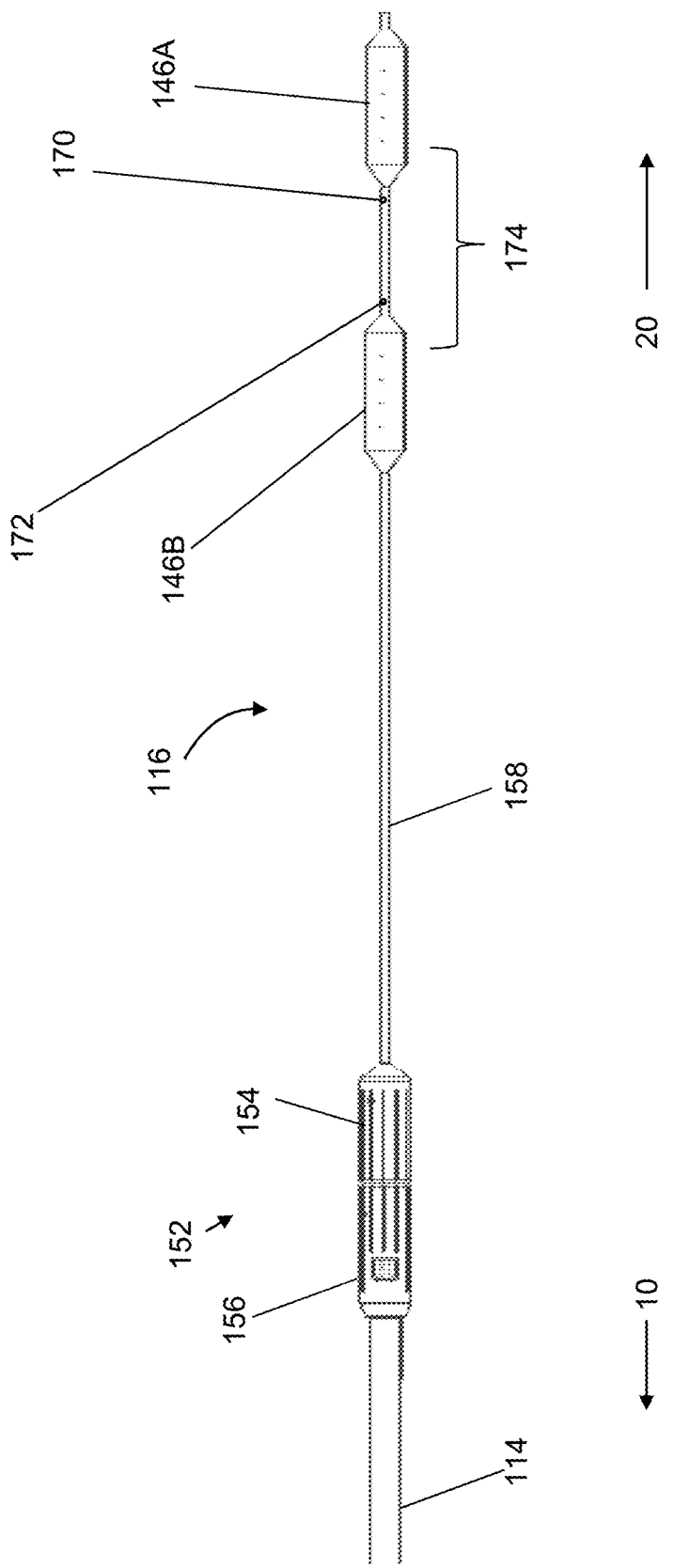
FIG. 7 is an illustrative view of a dual balloon lumen isolation catheter configuration according to an embodiment of the invention.

As depicted in FIG. 7, the catheter 116 may also be configured to include two individual balloons 146 disposed at different axial positions along the catheter shaft 158. For example, a first balloon 146A may be disposed distally of a second balloon 146B. In such an arrangement, both of the first and second balloons 146A, 146B can be inflated within the lumen of the patient's esophagus to create a contained region 174 along the length of the esophagus. Fluid may be directed out of the catheter 116 via supply/outflow port 170 and into the contained region 174 of the esophagus, coming into direct contact with and filling the portion of the esophagus 174. The fluid may then be returned to catheter 116 via return/inflow port 172, and conducted through catheter 116 and umbilical 114 to the console 102 or to be collected in a separate container for disposal. Collection of fluid following circulation to the catheter 116's distal end 20 or tip may be desired particularly when using the dual balloon 146A, 146B isolation catheter, in which the fluid comes into direct contact with the esophagus tissue.

Figure 8:
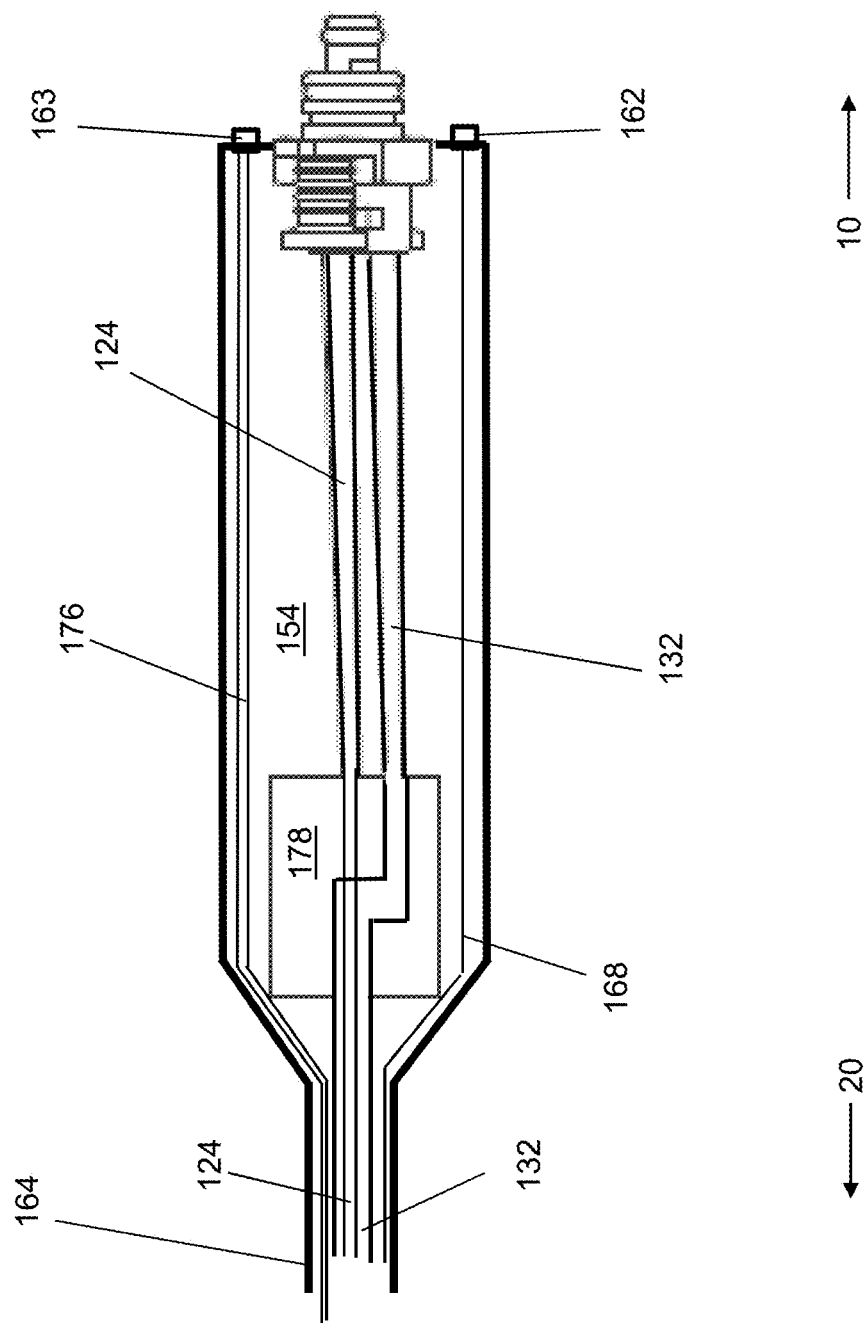
FIG. 8 is an illustrative view of the catheter handle located at the proximal end of the catheter according to an embodiment of the invention.

At the proximal end of the catheter assembly 116 is a handle assembly 152, shown in FIG. 7 and in greater detail in FIG. 8. The handle assembly 152 is made up of a proximal handle end 154 of catheter 116 which interconnects with distal handle end 156 of umbilical 114, e.g., via quick connect connection. Handle assembly 152 further includes a connection 162 for a communication relay (e.g. wires 168) from the catheter sensors 166, and a connection 163 for the balloon-like heat exchange vessel 146's inflation and deflation vacuum line 176. The handle assembly 152 may also house a coaxial tubing converter assembly 178, allowing for the transition from a co-axial "tube within a tube" configuration within catheter 116 to a side by side or substantially parallel tubing configuration for connection to the umbilical 114. The catheter handle 154 shown in FIG. 8 may connect at its proximal end to the distal handle end 156 of the umbilical 114 (FIGS. 7 and 9), which provides for the interconnection of the catheter 116 to the console 102 (FIGS. 1-2), although in other embodiments the umbilical 114 and catheter 116 may be an integrated single unit for connection to the console 102.

As depicted in FIG. 9, the umbilical 114 assembly may consist of a proximal end handle/connector 180 containing a connection point 186 (quick connect or other), an umbilical shaft 182 which may be covered with an outer sheath 184, and a distal catheter interconnection handle 156. The umbilical 114 may include a side by side supply 124 and return 132 line configuration which is contained within outer umbilical sheath 184 (FIG. 10). The umbilical shaft 182 may also contain a series of temperature, sensor and system control wires 168 which run the length of the umbilical 114. As described above with respect to the catheter 116, the lumen 160 within the outer sheath 184 can serve as the inflation/deflation path/tube 176 for inflation/deflation control of the balloon-like heat exchange vessel 146 at the distal end 20 of the catheter 116 (FIG. 6). In other embodiments, however, a third dedicated tube 176 may be provided for this purpose (FIG. 8). As shown in FIG. 10, the distal end 20 of the umbilical 114 contains an umbilical handle 156 which contains a connection point 188 (quick connect or other) for interconnection to the catheter handle 154. The distal handle end 156 of the umbilical 114 may also contain connection points 190 allowing for temperature and relay of information from sensors 166 from the catheter 116 to the console 102, as well as connection points 192 for inflation and deflation control. The handle assembly 152 (FIG. 7) may also include a control and display panel 194 disposed on, e.g., a radially outer surface of umbilical handle end 156 (FIG. 10). The control panel may include a control mechanism such as a switch or button 189 for user control of fluid flow, inflation/deflation of balloon-like heat exchange vessel 146 (FIG. 6), or other function. The panel 194 may also display readouts of one or more parameters such as fluid or tissue temperature, flow rate, pressure, or other parameters. Panel 194 may be in signal communication with system control and monitoring center 148 (FIG. 2) via a signal pathway 195 which, like wires 168, may include any type of wired or wireless communication.

The proximal end 10 of the umbilical 114 may include a connection 180 to console 102 (FIGS. 1-2), shown in FIG. 11. As with the distal end 20, the proximal end 10 of the umbilical 114 may include a fluid connection assembly (e.g., quick connect) 186, connection points 190, 192 as described above for connecting the fluid and electrical components catheter 116 with console 102, for relaying information from the sensors 166 (FIG. 6) and control and display components 194 (FIG. 10), and for enabling inflation and deflation control, and a control and display connection 193 for connecting panel 194's signal pathway 195 with console 102.

Figure 12:
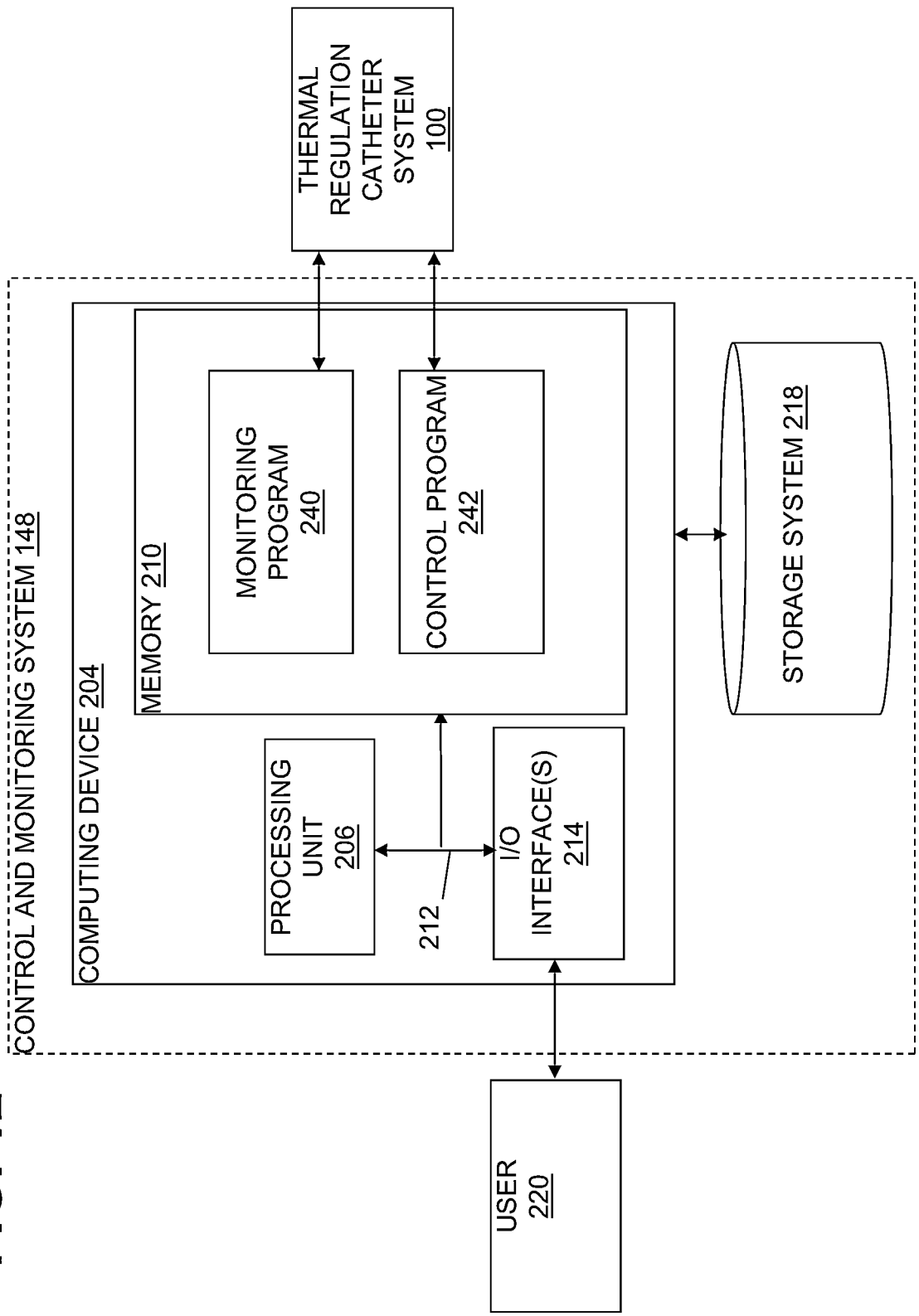
FIG. 12 is a schematic drawing of aspects of the control and monitoring system of FIG. 2, according to an embodiment of the invention.

FIG. 12 illustrates aspects of the control and monitoring center 148 (FIG. 2) in greater detail. As shown in FIG. 12, control and monitoring center 148 includes a computing device 204 that performs processes described herein in order to monitor system parameters such as time (e.g., elapsed), temperature of fluid or tissue, and fluid flow rates, and to control, adjust, or regulate the system parameters in accordance with user objectives.

Computing device 204 is shown including a processing unit 206 (e.g., one or more processors), a memory 210, a storage system 218 (e.g., a storage hierarchy), an input/output (I/O) interface component 214 (e.g., one or more I/O interfaces and/or devices), and a communications pathway 212. In general, processing unit 206 executes program code, such as monitoring program 240 and control program 242, which are at least partially fixed in memory 210. To this extent, processing unit 206 may comprise a single processing unit, or be distributed across one or more processing units in one or more locations.

Memory 210 can also include local memory, employed during actual execution of the program code, bulk storage (storage 218), and/or cache memories (not shown) which provide temporary storage of at least some program code in order to reduce the number of times code must be retrieved from bulk storage 218 during execution. As such, memory 210 may comprise any known type of data storage and/or transmission media, including magnetic media, optical media, random access memory (RAM), read-only memory (ROM), a data cache, a data object, etc. Moreover, similar to processing unit 206, memory 210 may reside at a single physical location, comprising one or more types of data storage, or be distributed across a plurality of physical systems in various forms, included, but not limited to a primary host site and/or a subscription backup site.

While executing program code, processing component 206 can process data, which can result in reading and/or writing transformed data from/to memory 210 and/or I/O component 214 for further processing. Pathway 212 provides a direct or indirect communications link between each of the components in control and monitoring system 148. I/O interface component 214 can comprise one or more human I/O devices, which enable a human user 220 to interact with control and monitoring system 148 and/or one or more communications devices to enable a system user 220 to communicate with control and monitoring system 148 using any type of communications link.

To this extent, monitoring program 240 and control program 242 can manage a set of interfaces (e.g., graphical user interface(s), application program interface, and/or the like)

that enable human and/or system users 220 to interact with monitoring and control programs 240, 242. Further, monitoring program 240 can manage (e.g., store, retrieve, create, manipulate, organize, present, etc.) the data collected during monitoring using any solution.

In any event, control and monitoring system 148 can comprise one or more general purpose computing articles of manufacture 204 (e.g., computing devices) capable of executing program code, such as monitoring and control programs 240, 242, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, monitoring and control programs 240, 242 can be embodied as any combination of system software and/or application software. As discussed herein, monitoring program 240 enables control and monitoring system 148 to implement monitoring of operational parameters of thermal regulation catheter system 100 or tissue on which system 100 is being used; and control program 242 enables control and monitoring system 148 to implement user-initiated or automatic adjustments to operational parameters, which may be made either independently or in dependence upon operational parameters as monitored by monitoring program 240.

Figure 13:
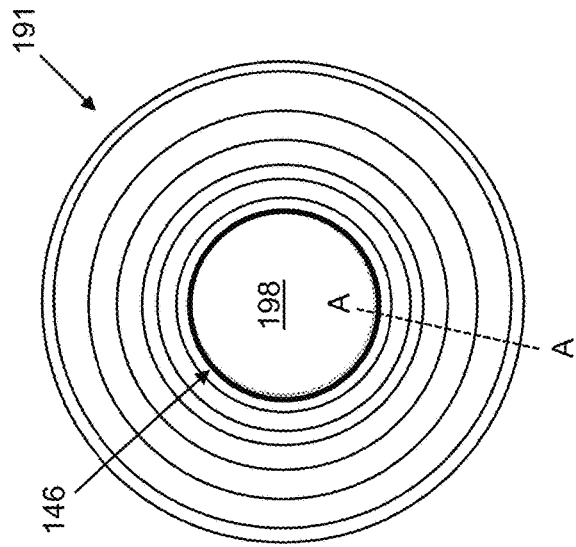
FIG. 13 is an illustration of the catheter in place within the esophagus during use, according to an embodiment of the invention.
Figure 14:
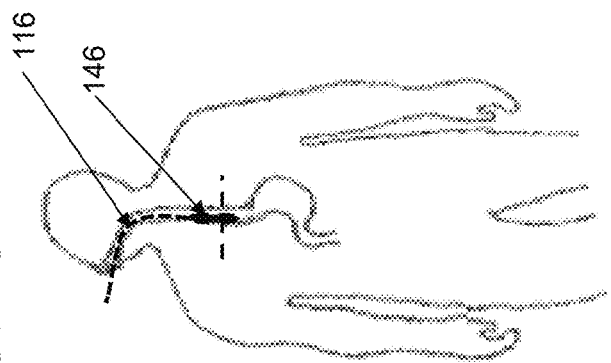
FIG. 14 is a cross sectional illustration the catheter in place within the esophagus during use as in FIG. 13, according to an embodiment of the invention.
Figure 16:
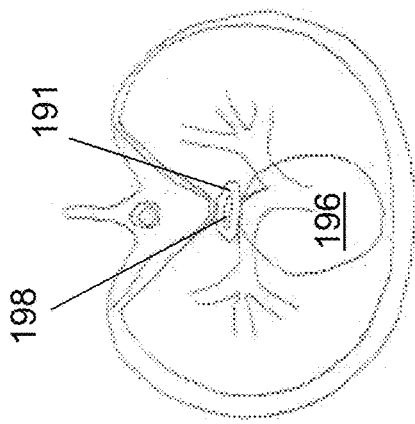
FIG. 16 is a cross sectional illustration of the esophagus and adjacent organs.
Figure 15:
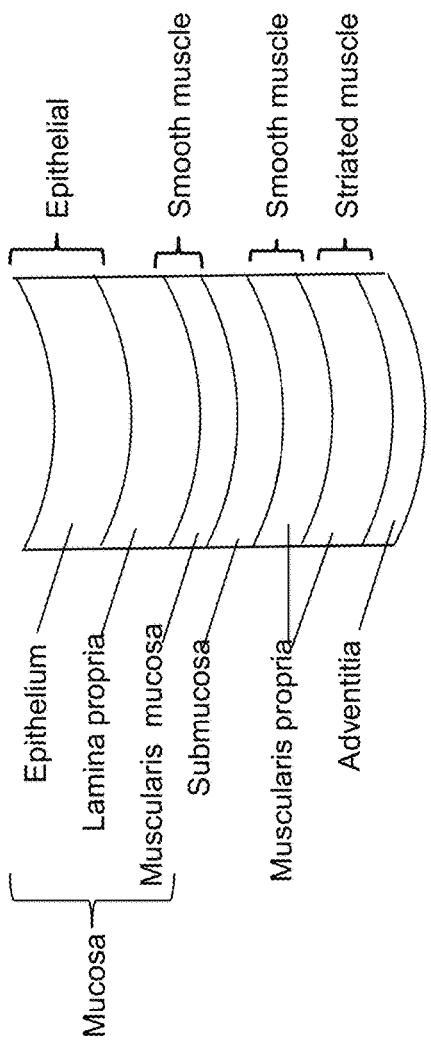
FIG. 15 is an illustration of the layers of the esophagus shown in FIG. 14 along line A-A.

During a cardiac ablation operation, catheter 116 is inserted through the mouth or nasal passage of a patient and positioned within the esophagus 191 adjacent to the heart 196, as shown in FIGS. 13-15. The proximity of the heart 196 and esophagus 191 is more clearly shown in FIG. 16. Positioning of heat exchange vessel 146 within the esophageal lumen 198 (FIG. 14) can be accomplished via any means of visualization including ultrasound, videoscopy, MRI, CT, fluoroscopy, distance gradient markings on the catheter, or any other means of visualization. Once in position as shown in FIG. 13, the fluid flow is activated by opening the flow control valve 128 on the console 102, allowing fluid to flow from the reservoir 106 (FIG. 2) to the catheter 116. Once flow is activated, the balloon-like heat exchange region tip 146 inflates, resulting in substantially circumferential contact between balloon heat exchange vessel 146 and the inner wall of the esophageal lumen 198, as shown in FIG. 14. Alternatively, only a portion of the esophageal wall may be contacted, depending on the configuration of the balloon heat exchange region of the catheter 116 (FIG. 13). In either case, when the balloon heat exchange vessel 146 comes into contact with interior wall surface of the esophageal lumen 198, heat exchange between the tissue and fluid occurs across the wall of balloon heat exchange vessel 146. This heat exchange results in either a heating or cooling of the esophagus tissue depending on the temperature of the fluid being circulated. The fluid is then circulated out of balloon heat exchange vessel 146 and back to console 102.

The fluid temperature within reservoir 106 may be set anywhere in the range from about −30° C. to about +50° C. depending on intended use, either with freezing or heat-based ablation devices, or as an ablation device itself. While this represents an exemplary range, depending on the strength, duration, and type of the ablation energy being applied and the translation of these temperatures into the esophagus, the use of fluid temperatures above or below this range may be desirable and may be adjusted at any point during operation. The temperature of the fluid within reservoir 106 and the heat exchange vessel 146 as well as the tissue/heat exchange region interface can be monitored in real-time through intergraded thermocouples or other sensors 166, located at various positions within the console 102 and catheter 116. Fluid flow rate, pressure, temperature, and level can also be measured at various points within the system. This series of monitoring sensors allows for the relay of information to an operator via control and monitoring system 148 during the procedure allowing for in procedure adjustment, either user-controlled or automated, of the device (temperature, flow, etc.) as needed.

In one example, the device may be used in a protective capacity, such as in conjunction with cardiac ablation procedures (e.g., heat-based or cryoablation). Exemplary fluid temperature ranges may be, e.g., from about −10° C. up to about 45-50° C., and particularly, in the range of about +30° C. to +50° C. for use in tissue warming during a cryoablation procedure, and in the range of −20° C. to 10° C. for use in tissue (e.g., esophageal tissue) cooling during a heat-based ablation procedure (e.g., a heat-based cardiac ablation procedure). Fluid temperatures above or below the indicated ranges may be utilized depending on the energy source and the desired outcome. For instance, during a heat-based ablation procedure such as, e.g., RF or HIFU, a cool or cold fluid ranging from −20° C. to 10° C. may be circulated within the heat exchange vessel 146. By providing a heat source/sink within the esophagus, a counter thermal gradient is created within the esophageal tissue. This keeps the tissue from experiencing lethal temperatures, thereby reducing or eliminating esophageal injury and the development of an atrialespohageal fistula following cardiac ablation therapy. In another example, the device may be used in conjunction with cardiac cryoablation procedures. A warmed fluid ranging in temperature of +30° C. to +50° C. may be circulated within the heat exchange vessel 146 to provide heating to the tissue to prevent excess freezing and resultant esophageal injury. During a cardiac cryoablation procedure when the cardiac wall and esophagus are in close proximity, during a typical 3-5 min freeze interval the esophagus wall can be frozen in the absence of the described device. For example, assessment of the thermal distribution in an ex vivo porcine cardiac and esophageal tissue model illustrate that temperatures of the inner wall of the esophagus can reach below −20° C. within a few minutes, which is highly injurious (FIG. 17, 211). As indicated in FIG. 17 a series of experiments were conducted using a porcine cardiac and esophageal model with (solid lines 310, 312, 313) and without (dotted lines 311, 314, 315) the application of the thermal regulation catheter system 100. Temperatures at the probe and cardiac tissue interface with 313 and without 315 and cardiac and esophagus tissue interface with 312 and without 314 the thermal regulation catheter system 100 were highly similar. Temperatures of the esophagus tissue surface differed significantly with 310 and without 311 the thermal regulation catheter system 100.

In a clinical setting, a repeat or dual freeze is often utilized in cardiac cryoablation procedures to assure cardiac tissue destruction. This procedure of applying a dual freeze insult to the esophagus can result in enhanced lethality even when temperatures within the esophagus only reach 0° C. or warmer. When the catheter 116 is applied in conjunction with cardiac cryoablation, the temperature of the wall of the esophagus may be maintained above freezing in a non-lethal thermal range during the entire procedure, thereby preventing esophageal injury. For instance, in the ex vivo porcine model, when the esophagus protection catheter was applied with the fluid reservoir temperature set to +40° C., a minimum temperature of +7° C. was measured at 1 mm below the inner surface of the model esophagus tissue wall during a 5 minute freeze procedure (FIG. 17, 310). This represented a temperature difference greater than 37° C. between the non-protected 311 and protected conditions 310 in the ex vivo model (>−30° C. without the catheter balloon vs. +7° C. with the catheter balloon). Further, while the temperature of the esophagus was affected, the temperature within the model cardiac tissue (inner probe/cardiac tissue interface 313 and 315 and outer cardiac/esophagus interface 312 and 314 temperatures) was not significantly impacted by the use of the thermal regulation catheter and was still able to deliver a highly ablative dose to the model cardiac tissue.

In another embodiment, the device may be used to perform ablation therapies, independently of another treatment modality. In such an example, fluid in reservoir 106 may be heated to a temperature of 50° C. or greater (for heat-based ablation) or cooled to −20° C. or colder (for cryoablation). For instance, this may be desired when the thermal regulation system is utilized to treat disease states such as esophageal cancer, Barrett's esophagus, gastric reflux disease or other indications.

Once a procedure is completed, the flow of fluid to the catheter 116 is stopped and the inflatable balloon-like heat exchange vessel 146 can be deflated prior to removal from the esophagus, using vacuum pump 135 in console 102, which is in fluid connection with heat exchange vessel 146 via vacuum line 176 (FIG. 8), connection port 144 on console 102, vacuum control valve 138, and vacuum line 142 (FIG. 2). In another embodiment, the catheter can simply be removed from the esophagus once fluid flow is stopped as the balloon naturally loses its form and partially deflates.

While the above system and method is described in reference to esophageal tissue protection during cardiac ablation therapy, the system (console 102, umbilical 114, and catheter 116) can be configured for use in any type of tissue ablation procedure wherein the protection of surrounding adjacent non-targeted tissues is desired and/or where the avoidance of collateral damage to surrounding tissue is desired. The device may be used, for example, for the treatment of multiple disease states including any type of cardiac arrhythmia or other tissue ablation.

The embodiments of the present invention may be modified to take the shape of any device, container, apparatus, or vessel currently used in industry. As disclosed herein, the catheter or probe of the invention may be of any size, shape, or dimension. The device may be a single use disposable unit, or may be a multi-use/reusable part that is capable of being sterilized between patient treatments. In one embodiment, the umbilical 114 coupling the catheter 116 to the console 102 may extend up to about 10-12 feet or more, although any length may be possible as designed for particular therapies and treatments. Shorter dimensions may be better suited where attached tubing, removable, detachable, or disposable parts are integrated in the design. Specifically, cylindrical or alternative structural designs may be used in the system for improved catheter/probe access to a tissue target. Further, any rearrangement of the tubes/lines in combination with the components of the above system may take many forms and be of any size, shape, or passageway.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A system comprising:
   a reservoir configured to contain and hold a volume of fluid to supply the system;
   a first temperature sensor within or affixed to the reservoir;
   a catheter including a shaft and a first heat exchange vessel at a distal tip of the shaft;
   a supply line configured to provide the fluid from the reservoir to the first heat exchange vessel; and
   a return line configured to conduct the fluid from the first heat exchange vessel to the reservoir,
   wherein the reservoir, the supply line, the catheter, and the return line form a fluid closed loop;
   a heating element disposed within or adjacent to the reservoir, the heating element being configured to achieve and maintain a fluid temperature within the reservoir of up to about 50° C.;
   a cooling element disposed within or adjacent to the reservoir, the cooling element being configured to achieve and maintain a first temperature of the fluid within the reservoir of about −30° C. or greater;
   a second temperature sensor within or affixed to the supply line, the second temperature sensor configured to monitor a second temperature of the fluid between the reservoir and the first heat exchange vessel;
   a third temperature sensor within or affixed to the return line, the third temperature sensor configured to monitor a third temperature of the fluid between the reservoir and the first heat exchange vessel; and
   a fluid supply pump located on the supply line between the reservoir and the catheter wherein the fluid supply pump is configured to control a flow of the fluid from the reservoir to the catheter.

2. The system of claim 1, wherein the first heat exchange vessel is inflatable and flexible.

3. The system of claim 2, wherein the first inflatable, flexible vessel is a single layer vessel bounded by a single membrane.

4. The system of claim 2, further comprising:
   a second heat exchange vessel, wherein the second heat exchange vessel is axially spaced and proximally disposed along the catheter shaft relative to the first heat exchange vessel; and a fluid outlet and a fluid inlet disposed along the catheter shaft between the first and the second heat exchange vessels, for outputting fluid supplied by the supply line, and for taking up fluid for return via the return line.

5. The system of claim 2, wherein the first inflatable, flexible vessel is a double layer vessel bounded by a membrane within a membrane.

6. The system of claim 1, further comprising at least one sensor in the first heat exchange vessel, wherein the sensor is one of: a temperature, pressure, flow rate, electrical conduction, electrical impedance, acoustic, infrared, ultrasound, or visual sensor, wherein the at least one sensor is in signal communication with a control and monitoring system.

7. The system of claim 1, wherein the reservoir is disposed within a console;
the console includes a connection port on an exterior thereof, the connection port providing a fluid connection for the supply line and the return line fluid between the reservoir and the catheter; and
the reservoir is provided with a fill line with a fill valve thereon, and a drain line with a drain valve thereon.

8. The system of claim 1, wherein the reservoir is disposed within a console, and the console includes:
a connection port on an exterior thereof, the connection port providing a fluid connection for the supply line and the return line fluid between the reservoir and the catheter; and
an inflation/vacuum pump disposed within the console, the inflation/vacuum pump being in fluid connection with:
an inflation supply line disposed within the catheter shaft, the inflation supply line being in fluid connection with the first heat exchange vessel for inflating the first heat exchange vessel, and
a vacuum return line in fluid connection with the first heat exchange vessel for deflating the first heat exchange vessel.

9. The system of claim 1, further comprising:
an umbilical tube disposed between the catheter and the reservoir, wherein the supply line and the return line run through the umbilical tube, and wherein the umbilical tube is flexible.

10. The system of claim 9, further comprising a handle assembly, the handle assembly including:
a catheter handle member disposed at a proximal end of the catheter; and
an umbilical handle member disposed at a distal end of the umbilical tube,
wherein the catheter handle member is connected to the umbilical handle member, providing fluid connections for the supply line and the return line from the reservoir to the first heat exchange vessel at the distal end of the catheter shaft.

11. The system of claim 10, further comprising a control pad disposed on the handle assembly, the control pad being configured to perform at least one of:
displaying a measurement obtained by at least one sensor disposed on the first heat exchange vessel, or
accepting user input to adjust an operating parameter of the system.

12. The system of claim 10, wherein the handle assembly further comprises a coaxial tubing converter assembly,
wherein the coaxial tubing converter assembly converts the supply line and the return line from being substantially side by side from the reservoir to the umbilical tube, to being substantially coaxial within the catheter.

13. The system of claim 10, wherein the handle assembly further comprises a quick connect connection between the catheter handle member and the umbilical handle member.

14. The system of claim 9, wherein the umbilical tube further comprises:
an inflation supply line disposed within the umbilical, the inflation supply line being in fluid connection with the catheter for inflating the first heat exchange vessel, and
a vacuum return line disposed within the umbilical, the vacuum return line being in fluid connection with the first heat exchange vessel for deflating the first heat exchange vessel.

15. The system of claim 14, wherein the inflation supply line and the vacuum return line collectively comprise a single lumen within the umbilical tube which is alternatively used for inflating or deflating.

16. The system of claim 1, wherein the heating element and the cooling element are separate elements.

17. The system of claim 1, wherein the heating element and the cooling element are a single heating and cooling coil disposed within the reservoir.

18. The system of claim 1 wherein the fluid supply pump is located in line with the supply line within the reservoir, or adjacent to the reservoir, wherein the fluid supply line is configured to circulate the fluid between the supply line, the return line, and the reservoir.

19. The system of claim 1 further comprising: a first flow rate sensor within or affixed to the supply line, the first flow rate sensor configured to monitor a first flow rate of the fluid between the reservoir and the first heat exchange vessel.

20. The system of claim 1 further comprising: a level sensor within or affixed to the reservoir configured to monitor a level of the fluid within the reservoir.

21. The system of claim 1,
wherein the reservoir is disposed within a console; the console includes a connection port on an exterior thereof, the connection port providing a fluid connection for the supply line and the return line fluid between the reservoir and the catheter, wherein the reservoir is provided with a fill line with a fill valve thereon, and a drain line with a drain valve thereon;
and further comprising:
an umbilical tube disposed between the catheter and the reservoir, wherein the supply line and the return line run through the umbilical tube, and wherein the umbilical tube is flexible;
a handle assembly, the handle assembly including:
a catheter handle member disposed at a proximal end of the catheter;
an umbilical handle member disposed at a distal end of the umbilical tube, wherein the catheter handle member is connected to the umbilical handle member, providing fluid connections for the supply line and the return line from the reservoir to the first heat exchange vessel at the distal end of the catheter shaft, wherein the handle assembly further comprises a coaxial tubing converter assembly,
wherein the coaxial tubing converter assembly converts the supply line and the return line from being substantially side by side from the reservoir to the umbilical tube, to being substantially coaxial within the catheter; and
wherein the heating element and the cooling element are a single heating and cooling coil disposed within the reservoir.

22. A system comprising:
a reservoir configured to contain and hold a volume of fluid to supply the system;
a first temperature sensor within or affixed to the reservoir;
a catheter including a shaft and a first heat exchange vessel at a distal tip of the shaft;
a supply line configured to provide the fluid from the reservoir to the first heat exchange vessel;
a return line configured to conduct the fluid from the first heat exchange vessel to the reservoir,
wherein the reservoir, the supply line, the catheter, and the return line form a fluid closed loop;
a heating element disposed within or adjacent to the reservoir, the heating element being configured to achieve and maintain a first temperature of the fluid within the reservoir of about 50° C. or greater;
a second temperature sensor within or affixed to the supply line, the second temperature sensor configured to monitor a second temperature of the fluid between the reservoir and the first heat exchange vessel;
a third temperature sensor within or affixed to the return line, the third temperature sensor configured to monitor a third temperature of the fluid between the reservoir and the first heat exchange vessel,
a level sensor within or affixed to the reservoir configured to monitor a level of the fluid within the reservoir; and
a fluid supply pump located on the supply line between the reservoir and the catheter wherein the fluid supply pump is configured to control a flow of the fluid from the reservoir to the catheter.

23. A system comprising:
a reservoir configured to contain and hold a volume of fluid to supply the system;
a first temperature sensor within or affixed to the reservoir;
a catheter including a shaft and a first heat exchange vessel at a distal tip of the shaft;
a supply line configured to provide the fluid from the reservoir to the first heat exchange vessel;
a return line configured to conduct the fluid from the first heat exchange vessel to the reservoir, wherein the reservoir, the supply line, the catheter, and the return line form a fluid closed loop;
a cooling element disposed within or adjacent to the reservoir, the cooling element being configured to achieve and maintain a first temperature of the fluid temperature within the reservoir of about −30° C. or greater;
a second temperature sensor within or affixed to the supply line, the second temperature sensor configured to monitor a second temperature of the fluid between the reservoir and the first heat exchange vessel;
a third temperature sensor within or affixed to the return line, the third temperature sensor configured to monitor a third temperature of the fluid between the reservoir and the first heat exchange vessel;
a level sensor within or affixed to the reservoir configured to monitor a level of the fluid within the reservoir; and
a fluid supply pump located on the supply line between the reservoir and the catheter wherein the fluid supply pump is configured to control a flow of the fluid from the reservoir to the catheter.

* * * * *